United States Patent [19]

Beaty et al.

[11] Patent Number: 5,685,715
[45] Date of Patent: Nov. 11, 1997

[54] SELF-INDEXING TRANSFER IMPRESSION COPING

[76] Inventors: Keith D. Beaty, 3 Old Meadow Way, Palm Beach Garderns, Fla. 33418; Curtis E. Jansen, 712 Sandpiper Way, North Palm Beach, Fla. 33408; Dan Paul Rogers, 10102 Yeoman La., Royal Palm Beach, Fla. 33411

[21] Appl. No.: 401,801
[22] Filed: Mar. 10, 1995
[51] Int. Cl.⁶ .................. A61C 13/12; A61C 13/225; A61C 8/00
[52] U.S. Cl. ........................... 433/173; 433/214
[58] Field of Search ................... 433/172, 173, 433/174, 175, 176, 214, 213

[56] References Cited

U.S. PATENT DOCUMENTS 5,312,254   5/1994   Rosenlicht .................. 433/173

OTHER PUBLICATIONS

Brånemark System, Product Catalog Prosthetics 1991, Nobelpharma (3 pages).
Prosthetic Catalog, 1993, Implant Innovations, Inc. (3 pages).
IMTEC Hexed–Head™ Implant System, IMTEC Prosthetic Components, Spring 1993 Catalog (2 pages).
Implant Support Systems, Inc., Catalog Summer 1993 (2 pages).
Interpore International, Restorative Components, Price and Data Sheet, May, 1990 (2 pages).
Prosthetic Catalog, Impression Copings, Implant Innovations, Inc. (3 pages).
IMPLA–MED The Source, IMPLA–MED Prosthetic Components (Nov. 1992) (3 pages).

*Primary Examiner*—Cary E. O'Connor

[57] ABSTRACT

A dental transfer coping for taking a dental impression of a patient's case in which information about the rotational position of an installed implant around its axis is preserved has plural impression interlocking elements arrayed on its outer surface. These elements are rotationally indexed to the ant-rotation device of the implant, and are uniformly arrayed around the coping so that the coping can be removed from the impression and reinstalled in it in many rotational positions without losing the rotational information of the implant.

92 Claims, 4 Drawing Sheets

SELF-INDEXING TRANSFER IMPRESSION COPING

FIELD OF THE INVENTION

This invention relates to dental copings of the kind used in implant dentistry in cooperation with resilient impression materials to take an impression from which to make a model of an edentulous site where an implant has been installed. More particularly, the invention relates an improved coping designed to form in the impression material a socket which releasably holds the coping and will self-index the coping upon the latter being reinserted into the socket so as to keep and preserve axial-rotational orientation information, and to multiple copings similarly designed for use interchangeably in the same socket without losing such information.

BACKGROUND OF THE INVENTION

Fashioning a dental restoration for a patient who has been fitted with one or more dental implants begins with taking an impression of the patient's case. Dental implants have indexing means useful to interlock with corresponding index means in the components fitted to them when it is desired to prevent rotation of a component relative to the implant around the longitudinal axis of the implant. These indexing means frequently take the form of a boss or a recess having a hexagonal-shaped transverse section (commonly called a "hex"). The hex of an implant is also useful to screw an externally-threaded implant into an internally-threaded bore prepared in the patient's jawbone to receive it. Once an implant has become osseointegrated with the host bone it is necessary to preserve in the impression the information describing the axial orientation of its hex if that information is to be used in the restoration, in order to transfer that information to the model of the patient's case that will be made in the dental laboratory. The component used to effect this information transfer is commonly called a "transfer coping". Examples of transfer copings as found in the prior art are shown in U.S. Pat. No. 4,955,811 at FIGS. 5, 6 and 9. Each of these figures shows a transfer coping with a hex fitting for mating with an implant, and has a flat side for indexing axial orientation information in an impression. It is an object of the present invention to improve upon prior art transfer copings.

By its very nature impression material is resilient, and soft enough that it can be removed from the patient's mouth after it has set up, yet firm enough that it can preserve information imparted to it by an impression coping. If the coping is not a "pick-up" type (one that remains in the impression when the latter is removed from the patient's mouth) it will remain behind in the patient's mouth when the impression is removed, pulling the transfer coping out of the socket formed around it in the impression. Thereafter, in the dental laboratory, the transfer coping must be reinserted into that socket in order to make a stone model of the patient's case. The probability that the coping will go back into the impression socket with precisely the same axial-rotational orientation that it had when the impression was made will be enhanced if the person inserting the coping into the socket carefully lines up the flat surface on the side of the coping with the corresponding flat surface formed by the coping in the socket. If these two flat surfaces are not so aligned it becomes necessary to twist the coping around its longitudinal axis toward correct alignment. However, a person twisting such a coping in a resilient socket finds it difficult to sense when the two flat surfaces are in exact alignment. The present invention teaches a transfer coping that will self-index in its socket in the impression material.

GENERAL NATURE OF THE INVENTION

The invention provides a coping with a plurality of individual impression interlocking elements on its exterior side surfaces arrayed symmetrically around the axis of the implant extended through the coping when the coping is installed on the implant. When an impression is taken using this coping a socket is formed in the impression material having a receiving element for each of the coping's interlocking elements. The individual interlocking elements of the coping can each interlock with any of the receiving elements of the socket, thereby providing an equal plurality of positions around the axis in which the implant can be put back into the socket. If there are three interlocking elements on the coping and three receiving elements in the socket there will be three such positions, each 120 degrees from each of the others. More than three interlocking elements may be used in copings according to the invention; however, three elements have been found to be an optimum number. Copings according to the invention, like prior-art copings, use the hex-form mechanical anti-rotation coupling to implants, in order to be useful with existing implant systems. Accordingly, the copings are fitted at one end with either a socket or a boss having six flat sides, all the same size, arrayed in a circular locus around the axis of the implant.

In a preferred embodiment of the invention alternate pairs of these flat sides are each aligned with one of the coping's interlocking elements in a longitudinal plane that is parallel to that axis. This preferred arrangement provides a coping which will preserve the implant's orientation information when the coping is inserted into the impression socket in any one of the three angular positions described. Unlike the single-flat-surface orientation indexing means of the prior art, the plural-interlocking-element indexing means of the present invention executes a positive "snap-in" feel when the new coping is inserted into the impression socket. It has been found when inserting this new coping into the impression socket that upon twisting the coping to find a proper orientation it snaps into a proper-orientation position as the plural interlocking elements simultaneously find positions in receiving elements in the socket.

Additional objects and features of the invention will be apparent in the following description of exemplary embodiments of it with reference to the accompanying drawings. The scope of the invention is delineated in the claims that are appended to this application.

DETAILED DESCRIPTION OF THE DRAWINGS

Figure 1:
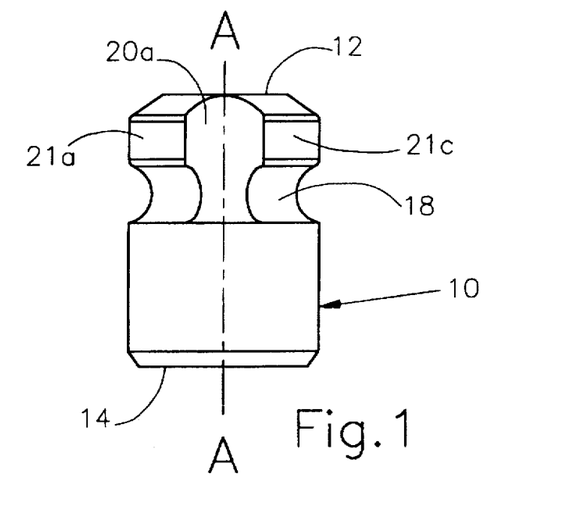
FIG. 1 is a side view of a coping according to the invention.
Figure 1A:
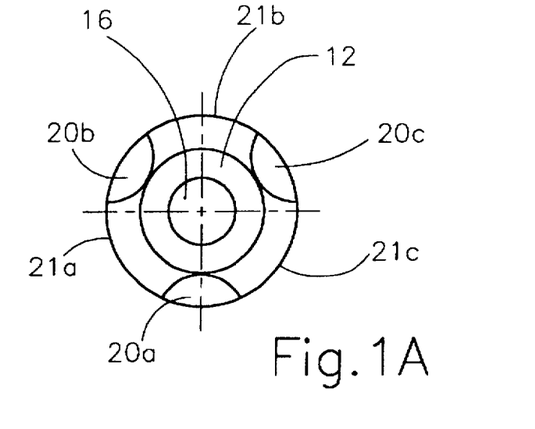
FIG. 1A is a top view of FIG. 1.
Figure 1B:
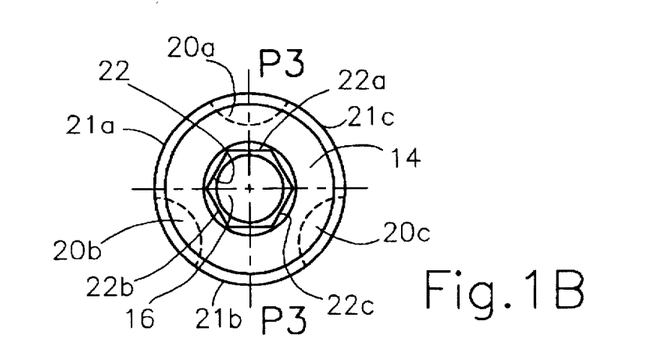
FIG. 1B is a bottom view of FIG. 1.
Figure 4:
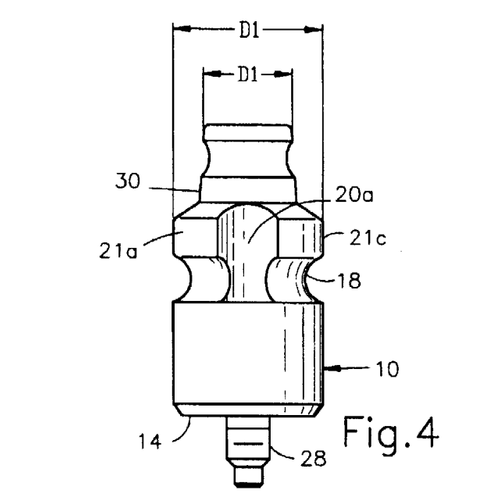
FIG. 4 is a side view of the coping and bolt fitted together.
Figure 4A:
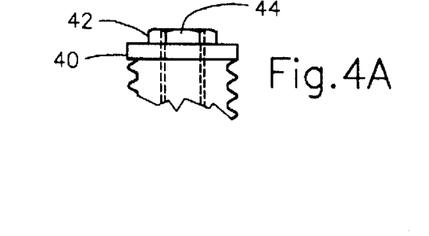
FIG. 4A schematically shows a typical implant in position for attaching the coping and bolt to it.

Referring generally to FIGS. 1–4A, inclusive, the illustrated coping 10 has a top end 12 and a bottom end 14, and a through passage 16 from one end 12 to the other 14. FIG. 1A is a view of the top end 12. FIG. 1B is a view of the bottom end 14. The coping 10 is tubular in form, symmetrical around its longitudinal axis A—A. A portion 18 of the outer surface of the coping is circumferentially recessed. Three longitudinal recesses 20a, 20b and 20c are symmetrically arrayed around the upper portion of the coping, extending from the circumferential recess 18 to the upper end 12. The recesses 18, 20a, 20b and 20c are all formed on a circular locus, but that is by way of example only. Recesses having other transverse-sectional shapes, such as rectangular and triangular, may also be used in copings of the invention. A hexagonal anti-rotation socket 22 of known form is located in the bottom end 14, symmetrical around the axis A—A. The through-passage 16 opens into this hexagonal socket. An attaching bolt 24 (FIG. 3) has a shaft 26 sized to fit (preferably snugly) in the through-passage 16, a threaded end 28 for engaging in a threaded bore 44 in an implant 40 (FIG. 4A), and a head 30 for manipulating the bolt, and for other uses to be presently described. As is shown in FIG. 4, the head 30 abuts the end 12 of the coping when the latter is fixed to the implant 40, which has a hexagonal boss 42 of known form to engage the socket 22.

Figure 2:
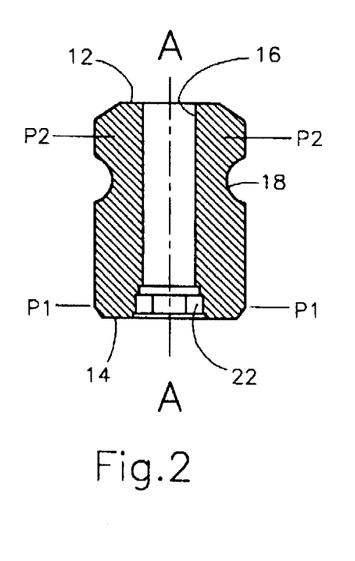
FIG. 2 is a longitudinal section through FIG. 1.
Figure 5:
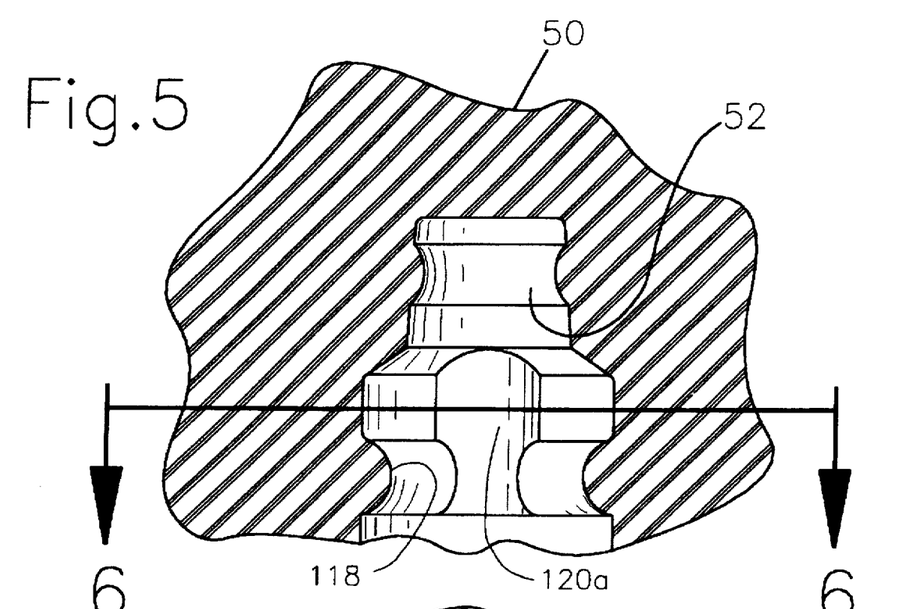
FIG. 5 is a section through impression material showing a socket formed by the coping of the invention.
Figure 6:
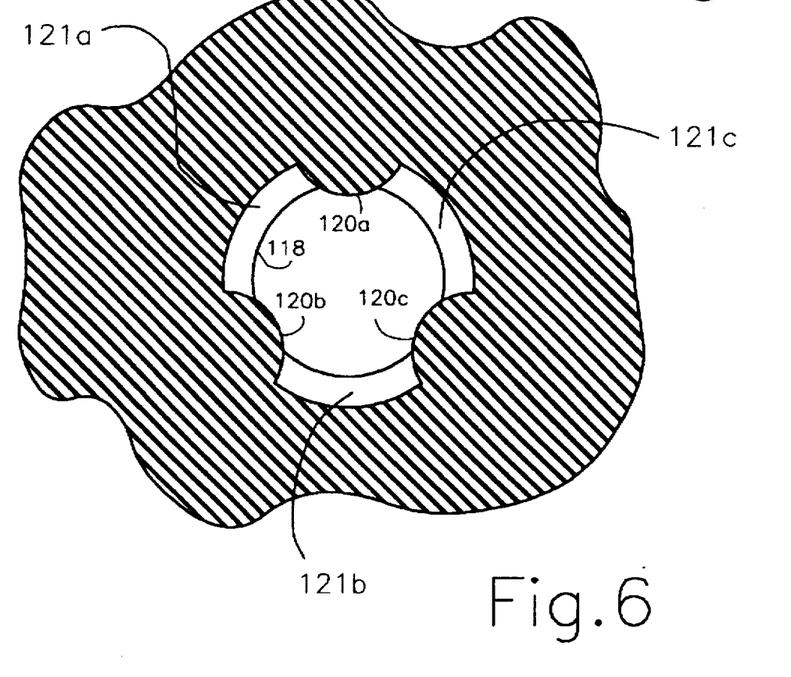
FIG. 6 is a sectional view of FIG. 5 taken on line 6—6.

The recesses 18, 20a, 20b and 20c form three projections 21a, 21b and 21c arrayed symmetrically around the axis A—A which serve as individual impression interlocking elements in impression material, shown in FIGS. 5 and 6. The socket 22 embraces a plane P1—P1 (FIG. 2). The projections 21a, 21b and 21c embrace a plane P2—P2 (FIG. 2) These planes are transverse to the axis A—A, and are spaced apart along that axis. Each of the longitudinal recesses 20a, 20b and 20c is aligned longitudinally with a specific one of the flat surfaces 22a, 22b or 22c of the hexagonal socket 22, in a plane that is parallel to the axis A—A. This is shown in FIG. 1B where plane P3—P3 is the alignment reference for recess 20a and flat surface 22a; this shows also that the recess 20a is thereby aligned also with the opposite flat surface of the socket 22. The projection 21b opposite the recess 20a is therefore aligned with the same flat surfaces of the socket as is the recess 20a. The same is true for the projection 21a opposite recess 20c, and for the projection 21c opposite recess 20b. Looking at FIG. 1B it is apparent that this figure can be rotated 120 degrees in either direction around the longitudinal axis A—A and the posture of the hexagonal shape of the socket 22 around the axis will remain unchanged. The impression interlocking elements 20a, 20b and 20c and the anti-rotation socket 22 are indexed for symmetry around the axis A—A.

The configuration of the transfer impression coping of the invention which employs three impression interlocking elements in cooperation with the customary hexagonal implant interlocking socket is deemed optimal, and is the preferred embodiment of the invention at the present time. It is to be understood that other embodiments are possible, and are intended to be embraced within the scope of the appended claims.

when the coping 10 and the attaching bolt 24 are assembled as shown in FIG. 4 they form a compact impression transfer coping assembly with additional advantages. The head 30 has a diameter D2 which is smaller than the diameter D1 of the coping. This combination forms a socket 52 in the impression material 50 (FIGS. 5 & 6) which is narrower at its interior end that it is at its open end. During reinsertion of the coping into the impression socket the head 30 can "feel" the entrance to the narrow end and guide the coping into the socket while the impression interlocking elements 21a, 21b and 21c are being manipulated around the axis A—A.

Referring now to FIGS. 5 and 6, when the impression material 50 sets up around the coping 10 and bolt head 30 an impression socket 52 is formed replicating in reverse the shape and size of the coping and the bolt head. Thus for the annular recess 18 there is an annular bulge 118, for each longitudinal recess 20a, 20b and 20c there is a longitudinal bulge 120a, 120b and 120c, and for each projection 21a, 21b and 21c there is a corresponding recess 121a, 121b and 121c. Whenever the coping is reinserted into the socket 52 each of the projections can occupy any of the corresponding recesses, thus replicating the three possible orientation positions of the coping described above with reference to FIG. 1B.

Figure 3:
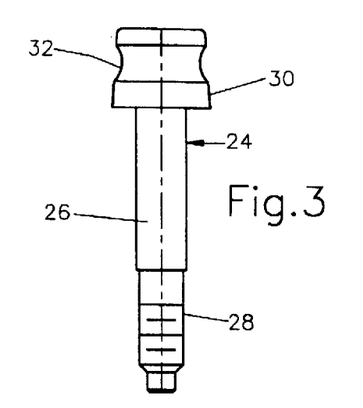
FIG. 3 is a side view of an attaching bolt for the coping.
Figure 3A:
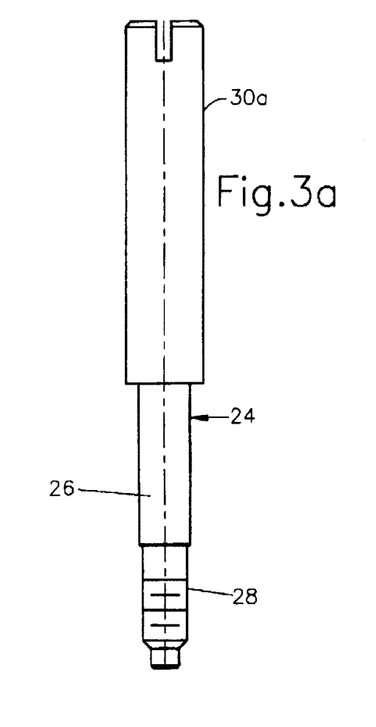
FIG. 3A is a side view of another attaching bolt.

The head 30 may take many forms. It may include a circumferential recess 32 as shown, for additional retention in the impression socket 52. It may omit any such recess. It may be shorter or longer than the head that is illustrated. It may have means to engage a driver for turning it. If the bore 16 is fitted with an internal shoulder (not shown) the shaft 26 may be altered to engage that shoulder, in which case the diameter of the head 30 may be reduced to the same as or less than the diameter of the shaft 26. If desired, the head may be extended in length, as shown at 30A in FIG. 3A, to enable the coping 10 to be used in a pick-up application.

The coping and head may take a somewhat conical or pyramidal form, which has an advantage when taking an impression of a case having two copings on divergent axes. In such a case, if the two copings are cylindrical they will have remote surfaces that diverge, making it difficult to remove the copings from an impression. The conical form made possible in the present invention prevents divergence of the remote surfaces over a wide range of divergent axes.

Owing to its self-indexing and self-guiding features, the impression transfer coping of the invention can be made in sizes that are unusually short. For example, the distance between the top end 12 and the bottom end 14 can be as small as about 5 mm. As is mentioned above, the dimensions of the bolt head 30 can be varied over a wide range without losing its self-guiding property; if that property is built into the coping body 10 the bolt head can be further diminished in size. Accordingly, in the claims that follow, the term "coping" is intended to encompass any structure or combination of structures that forms the impression socket 52, a unitary (one-piece) coping as well as a coping which includes a separate head such as the illustrated head 30.

Figures 7, 7A:
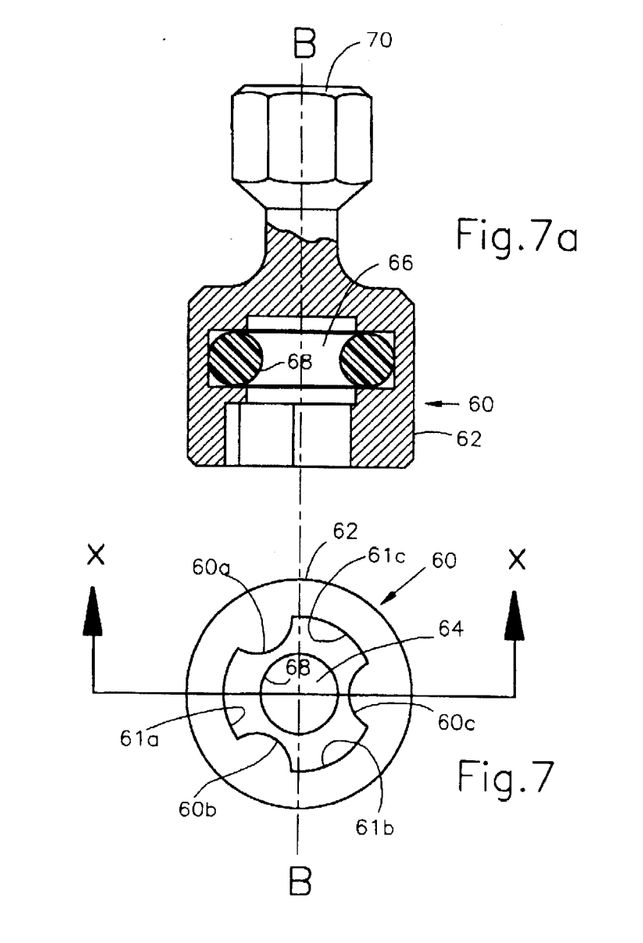
FIG. 7 is an end view of a driving tool.
FIG. 7A is a longitudinal section on line X—X of FIG. 7.

The plural individual impression interlocking elements of the invention may be used in combination with a wrench 60 illustrated in FIGS. 7 and 7A to drive a threaded implant into a suitable prepared bore in a patient's jawbone. The coping 10 is, for example, attached to an implant 40, as is suggested in FIGS. 4 and 4A. An implant with the coping and its bolt 24 attached can be delivered to a dentist in a sterile package (not shown), or the dentist can attach to coping and its bolt to an implant for use initially as an implant carrier. The wrench 60 comprises a tubular body having in its interior bore 64 a plurality of longitudinal bulges 60a, 60b and 60c, corresponding, respectively, to the bulges 120a, 120b and 120c in the impression socket 52 in FIG. 6. Between these bulges are three recesses 61a, 61b and 61c, corresponding, respectively, to the recesses 121a, 121b and 121c in FIG. 6. The tubular portion of the body 62 containing these bulges and recesses fits matingly over the portion of the coping 10 which has the longitudinal recesses 20a, 20b and 20c and the projections 21a, 21b and 21c, so that the bulges of the wrench fit one each into the recesses of the coping, and the recesses 61a, b and c of the wrench fit one each over the projections 21a, b and c of the coping, thus interlocking the wrench and the coping against relative rotation around their common axis B—B. Further into the hollow bore 64 the wrench has an annular groove 66 fitted with an O-ring 68 of resilient material such as rubber or plastic. Fitted to the exterior of the wrench, a distance axially away from the tubular body 62, is a six-sided (hex) head 70, of a kind useful for turning the wrench around its axis B—B.

Figure 8:
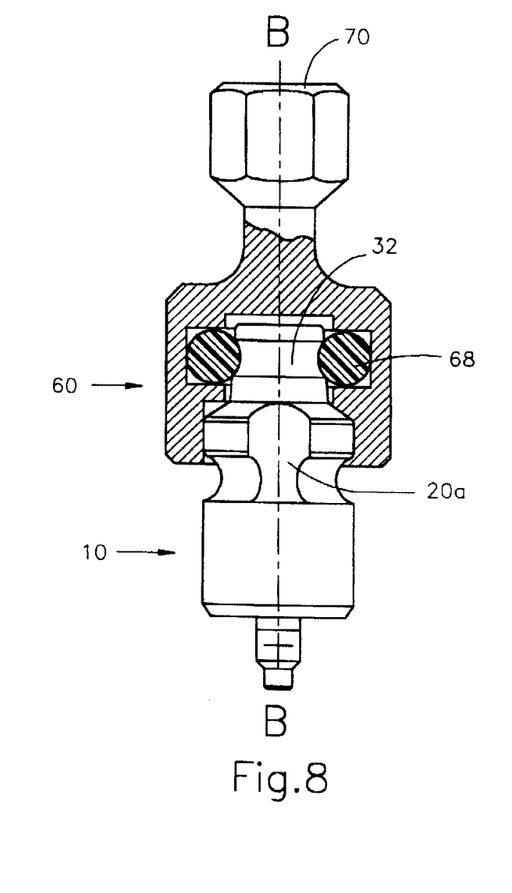
FIG. 8 shows the driving tool coupled to the coping of FIG. 4.

In use, as is shown in FIG. 8, the wrench fits over the coping 10 and the bolt head 30. The annular groove 32 is releasably grasped within the O-ring 68, which retains the coping in the wrench. Via the hex head 70 the wrench, and with it the coping 10, can be turned around the axis B—B. If the coping is attached to an implant the implant can thereby be turned into a surgically-prepared bore in the jawbone of a patient. A positive non-slipping lock against relative rotation around the axis B—B is established by the plural independent locking elements of the coping and the wrench, respectively, which is not found in the prior art. For example, in U.S. Pat. No. 5,312,254 it is proposed to use a wrench having a socket with a single flat land surface to engage and turn a coping of the kind shown in U.S. Pat. No. 4,955,811 mentioned above. For the same reasons that the coping of the present invention provides superior indexing in a socket formed by it in impression material, the wrench and coping combination herein disclosed provides superior interlocking for wrenching purposes. With this combination, an implant can be brought to the above-mentioned bore, started and screwed into it in a continuous uninterrupted procedure. There is no need to carry the implant to the site with a first implement and thereafter complete the installation with another implement, as is taught in the '254 patent.

We claim:

1. A self-indexing impression coping attachable on a common axis to a dental implant inserted into bone through an epithelial tissue layer and useful in cooperation with a resilient impression material to take an impression for making a model to produce a prosthetic tooth, said implant having first mechanical interlocking means fixed in orientation around said common axis, said self-indexing impression coping comprising:

second mechanical interlocking means for engaging said first mechanical interlocking means to prevent relative rotation between said coping and said implant around said common axis when said implant and said coping are attached together, each of said first and second mechanical interlocking means having a number "n">1 individual mechanical interlocking elements arrayed symmetrically around said common axis, said second mechanical interlocking means of said coping lying substantially in a first plane that is transverse to said common axis; and a number "m" of impression interlocking elements wherein said number "m" is chosen to be "n" or "n/2", said impression interlocking elements arrayed around said common axis to engage said impression material, said impression interlocking elements lying substantially in a second plane being transverse to said common axis and being axially separated from said first plane, and each of said impression interlocking elements being circumferentially aligned around said common axis with one of said second mating mechanical elements.

2. The coping according to claim 1 in which n=6 and m=3.

3. The coping according to claim 1 in which each of said second mechanical interlocking means is composed of six substantially identical flat surface elements forming a hexagon.

4. The coping according to claim 3 in which said number m is a number selected from the group consisting of 3 and 6.

5. The coping according to claim 1, wherein said coping is generally tubular and includes recesses on an outer surface thereof, said recesses forming said number m of said impression interlocking elements.

6. The coping according to claim 5, wherein each of said recesses is defined by a curved surface.

7. A combination of the coping according to claim 1 and an impression material forming a socket around said coping with a receiving element for each of said impression interlocking elements, said receiving elements being symmetric around said common axis.

8. The combination according to claim 7 in which n=6 and m=3.

9. The combination according to claim 7 in which each of said second mechanical interlocking means is composed of six flat surface elements forming a hexagon.

10. The combination according to claim 9 in which m is a number selected from the group consisting of 3 and 6.

11. The combination according to claim 7, wherein said receiving elements are circumferentially symmetric around said common axis.

12. The coping of claim 1, wherein said impression interlocking elements are arrayed circumferentially symmetrical around said common axis.

13. An impression coping for cooperating with a resilient impression material to take an impression for making a model of a region in a mouth adjacent to an implant that is installed in bone, said coping comprising:

a generally tubular first part having a through-passage extending therethrough along a central axis, said first part having an outer surface with a plurality of longitudinal recesses and a plurality of interlocking elements circumferentially symmetrical thereon for engaging said impression material and resisting the rotation of said generally tubular first part around said central axis when positioned within said impression material, each of said plurality of recesses separating adjacent ones of said plurality of interlocking elements; and a second part for coupling said first part to said implant, said second part having a shaft that is sized to fit in and through said through-passage with means at a first end of said shaft for restraining the movement of said first part relative to said implant and a head at the other end of said shaft for engaging said first part.

14. The impression coping according to claim 13 in which said head is substantially symmetrical around said shaft when said shaft is attached to said implant, and said head has an external diameter which is smaller than an external diameter of said generally tubular first part.

15. The impression coping according to claim 14 in which said head has an exterior surface with means for requiring force to move said head in an axial direction within said impression material, said force-requiring means including a recess.

16. The impression coping of claim 13, wherein each of said plurality of longitudinal recesses is defined by a curved surface and each of said plurality of interlocking elements has a curved exterior surface.

17. The impression coping of claim 16, wherein said curved exterior surfaces of said plurality of interlocking elements and said curved surfaces of said plurality of longitudinal recesses meet at substantially sharp corners.

18. The impression coping of claim 13, wherein said head of said second part extends substantially above said first part such that said impression coping is a pick-up coping.

19. The impression coping of claim 13, wherein head of said second part extends a short distance above said first part such that said impression coping is a transfer coping.

20. The impression coping of claim 19, wherein said head of said second part tapers inwardly in a direction away from said first part, said head having an outer surface with a recess thereon.

21. The impression coping of claim 13, wherein said first part has a length measured along said central axis of less than about 5.0 mm.

22. A dental impression coping for attachment to a root means embedded at a site within living jawbone, comprising:
   a body having an outer surface that is substantially symmetrical around an axis extending through said body, said body being non-rotationally attachable at a first end to said root means; and
   a plurality of individual impression interlocking elements being disposed circumferentially symmetric around said axis on said on its outer surface of said body, each of said plurality of individual impression interlocking elements having a curved exterior surface.

23. The coping according to claim 22, wherein said body includes an axially-directed bore therethrough for receiving bolt means to attach said body to said root means, said body further including anti-rotational means to provide said non-rotational attachment of said coping around said axis relative to said root means when said coping is attached to said root means.

24. The coping according to claim 23 wherein said impression interlocking elements and said anti-rotation means are indexed for symmetry around said axis.

25. The coping according to claim 24 wherein said impression interlocking elements include three projections and said anti-rotation means are six flat surfaces forming a hexagon, each of said three projections being circumferentially aligned with one of said six flat surfaces.

26. The combination of the coping of claim 22 and a wrench having a bore sized to receive said body of said coping, said wrench having in said bore an individual receptor for each of said impression interlocking elements for locking said wrench and said coping against relative rotation around said axis when said body is resident within said bore.

27. The combination according to clam 26 further including means to turn said wrench and said coping locked thereto around said axis.

28. The combination according to claim 26 further including means to releasably hold said coping within said bore.

29. The impression coping of claim 22, wherein said coping further includes means for forming a taper inwardly toward said axis in a direction away from a first end adjacent to said root means.

30. The impression coping of claim 29, wherein said taper-forming means includes said outer surface of said body.

31. The impression coping of claim 29, wherein said taper-forming means includes a head of screw disposed adjacent to a second end opposite said first end.

32. The impression coping of claim 22, wherein said curved exterior surfaces of said plurality of interlocking elements are at a constant radius from said axis.

33. The impression coping of claim 22, wherein said body has a length measured along said axis that is less than about 5.0 mm.

34. The impression coping of claim 22, wherein said curved exterior surfaces of said plurality of interlocking elements define a portion of said outer surface, adjacent ones of said plurality of interlocking elements being separated by a recess.

35. The impression coping of claim 34, wherein each of said recesses is defined by a curved surface.

36. The impression coping of claim 34, wherein each of said recesses meets an adjacent interlocking element at an intersection, said impression coping having at least six intersections.

37. The impression coping of claim 36, wherein each of said intersections is generally sharp.

38. A combination of a coping and a wrench, said coping comprising a body being substantially symmetrical around an axis extending therethrough, said body being attachable at a first end to another component and having an outer surface tapering inwardly toward said axis at a second end, said outer surface having a plurality of individual impression interlocking elements on said outer surface, said wrench having a bore sized to receive said body and having in said bore an individual receptor for each of said plurality of impression interlocking elements, for locking said wrench and said coping against relative rotation around said axis when said body is resident within said bore.

39. The combination according to claim 38 wherein said wrench includes means to turn said combination of said wrench and said coping around said axis.

40. The combination according to claim 39 in which said coping includes a bolt for fastening said body to another structure.

41. The combination according to claim 40 in which said another structure is a dental implant, said dental implant including means to engage said coping non-rotationally.

42. The combination according to claim 38 wherein said wrench includes means for releasably holding said coping within said bore.

43. The combination according to claim 42 in which said holding means includes an O-ring within said bore and an annular groove on said coping for interlocking within said O-ring.

44. The combination according to claim 43 in which said coping includes a bolt for fastening said body to another structure, and said bolt has a head on which said annular groove is disposed.

45. The combination of claim 38, wherein said plurality of individual impression interlocking elements are circumferentially symmetric around said axis.

46. An impression coping for making a model of a site in a human mouth adjacent to a root means that is disposed within living jawbone at said site, said impression coping comprising:
   a body having a central axis and outer surface therearound;
   means for locking said body non-rotationally relative to said root means; and
   means for holding impression material non-rotationally on said outer surface, said holding means including multiple elements disposed in circumferential symmetry around said central axis, each of said multiple elements being spaced from two adjacent multiple elements by a curved surface having in a cross-sectional view an arc length that is a substantial portion of a width of said body.

47. The impression coping of claim 46, further including means for attaching said body to said root means.

48. The impression coping of claim 46, further including a bolt extending through a central bore in said body for threadably engaging a threaded bore in said root means and attaching said body thereon.

49. The impression coping of claim 46, wherein said locking means includes a generally polygonal structure having a plurality of sides, each of said multiple elements being circumferentially aligned with one of said plurality of sides.

50. The impression coping of claim 46, wherein said body has a length measured along said central axis of less than about 5.0 mm.

51. The impression coping of claim 46, wherein each of said multiple elements has a curved exterior surface.

52. The impression coping of claim 46, wherein said body tapers inwardly toward said central axis from an end adjacent said root means to an opposing end of said body.

53. The impression coping of claim 46, wherein said curved surface has a negative curvature with respect to said central axis.

54. The impression coping of claim 53, wherein each of said multiple elements has a curved exterior surface, said curved exterior surface having a positive curvature with respect to said central axis.

55. The impression coping of claim 54, wherein said curved exterior surfaces of said multiple elements and said curved surfaces positioned therebetween meet at a sharp corner.

56. The impression coping of claim 54, wherein each of said multiple elements includes two side surfaces directed generally radially and being located on either said of said curved exterior surface, each of said two side surfaces meeting an adjacent one of said curved surfaces with at a smooth transition.

57. An impression coping for making a model of a site in a human mouth adjacent to a root means that is disposed within living jawbone at said site, said impression coping comprising:
    a body having a central axis; and
    a plurality impression interlocking elements extending radially outward from said body and being circumferentially spaced from one another, each of said plurality of impression interlocking elements being defined by three adjacent longitudinal surfaces, two of said three adjacent surfaces having portions which generally extend in a radial direction with respect to said axis, the other of said three adjacent surfaces extending in generally a circumferential direction with respect to said axis, said other of said three adjacent surfaces being disposed between said two of said three adjacent surfaces.

58. The impression coping of claim 57, wherein said other of said three surfaces is curved.

59. The impression coping of claim 58, wherein said other of said three surfaces has a positive curvature with respect to said axis.

60. The impression coping of claim 57, wherein said two of said three surfaces is curved.

61. The impression coping of claim 57, wherein said plurality of impression interlocking elements are circumferentially symmetrical around said axis.

62. The impression coping of claim 57, further including anti-rotational locking elements at one end of said body for restraining the rotational movement of said body relative to said root means, each of said three surfaces being circumferentially aligned with one of said anti-rotational locking elements.

63. The impression coping of claim 57, wherein the number of said plurality impression interlocking elements is three, said three impression interlocking elements being spaced at 120° from each other around said axis.

64. An impression coping assembly for making an impression of a site in a mouth, said impression coping assembly for attaching to a root means located in jawbone at said site and having a hexagonal fitting and a threaded bore, said impression coping assembly comprising:
    a tubular body having a first end, a second end, and a bore extending between said first end and second end along a central axis of said tubular body, said first end being adjacent to said root means and having a hexagonal portion for engaging said hexagonal fitting of said root means, said body having an external surface including three recesses defining three external projections having curved exterior surfaces, each of said external projections being positioned at 120° relative to said central axis from the other two of said external projections and being aligned with one surface of said hexagonal socket; and
    an elongated screw for insertion through said bore of said tubular body and attaching said body to said root means, said elongated screw having a threaded end for engaging said threaded bore and a head for engaging said tubular body.

65. The impression coping assembly of claim 64, wherein said head extends substantially beyond said tubular body such that said impression coping assembly acts as a pick-up coping.

66. The impression coping assembly of claim 64, wherein said head terminates a short distance above said tubular body such that said impression coping assembly acts as a transfer coping.

67. A kit of dental components for use in providing a single tooth restoration at a site in living jawbone, said kit comprising:
    a dental implant to be inserted into said jawbone at said site, said dental implant having a fitting at one end and an internally threaded bore centered on an axis;
    an impression coping including a tubular body having a first end, a second end, and a bore extending between said first and second ends along a central axis of said tubular body that is substantially co-linear with said axis of said dental implant, said first end having means for engaging said fitting and holding said impression coping nonrotationally on said fitting of said dental implant, said tubular body having an external surface including a plurality of impression elements for engaging impression material and holding said impression coping non-rotationally within said impression material, said impression elements being disposed in circumferential symmetry around said axis;
    an elongated screw for insertion through said bore of said tubular body and attaching said body to said dental implant, said elongated screw having a threaded end for engaging said internally threaded bore of said dental implant; and
    a wrench for coupling to said impression coping, said wrench having a plurality of individual receptors for receiving a corresponding one of said plurality of impression elements, said wrench having means for rotating said coping around said central axis, said wrench capable of inserting said dental implant into said jawbone when said dental implant is attached to said impression coping.

68. The kit of claim 67, wherein said means for engaging and holding said impression coping nonrotationally on said firing includes multiple flat surfaces, each of said impression elements being circumferentially aligned with one of said multiple flat surfaces.

69. The kit of claim 67, wherein said wrench includes means for retaining said impression coping therein.

70. The kit of claim 69, wherein said retaining means includes an O-ring.

71. The kit of claim 70, wherein said elongated screw includes a head having a recess, said O-ring engaging said recess.

72. The kit of claim 67, wherein said wrench is capable of inserting said dental implant into its final position within said jawbone.

73. The kit of claim 67, wherein said wrench encapsulates a substantial portion of said impression coping adjacent to said second end.

74. A method of installing a dental implant into a final position at a site having a bore within living jawbone, said method comprising the steps of:
providing a set of dental components including said dental implant, an impression coping being attached to said dental implant, and a wrench connected to said impression coping, said impression coping having a plurality of impression elements for engaging impression material and holding said impression coping non-rotationally within said impression material, said plurality of impression elements being disposed in circumferential symmetry around said axis, said wrench having a plurality of individual receptors for receiving a corresponding one of said plurality of impression elements;
guiding said dental implant to said site and into said bore by manipulating said wrench to which said impression coping and said dental implant are connected; and
using said wrench to insert said dental implant into said final position in said bore within jawbone at said site.

75. The method of claim 74, wherein said dental implant is externally threaded and said step of using said wrench to insert said dental implant includes the step of rotating said wrench.

76. The method of claim 74, wherein said wrench includes means for retaining said impression coping therein.

77. A method of installing a dental implant into a final position at a site having a bore within living jawbone, said method comprising the steps of:
providing a set of dental components including said dental implant, an impression coping attached to said dental implant, and a wrench connected to said impression coping, said impression coping having at least one impression element for engaging impression material and holding said impression coping non-rotationally within said impression material, said wrench having a receptor for receiving said at least one impression element;
guiding said dental implant to said site and into said bore by manipulating said wrench to which said impression coping and said dental implant are connected; and
using said wrench to insert said dental implant into said final position within said jawbone at said site.

78. The method of claim 77, wherein said dental implant is externally threaded and said step of using said wrench to insert said dental implant includes the step of rotating said wrench.

79. The method of claim 77, wherein said wrench includes means for retaining said impression coping therein.

80. A method of taking an impression of a site in the mouth where a tooth restoration is to be positioned to replace a natural tooth, said method comprising the steps of:
providing a set of dental components including a dental implant, an impression coping attached to said dental implant, and a wrench connected to said impression coping, said impression coping having at least one impression element for engaging impression material and holding said impression coping non-rotationally within said impression material, said wrench having a receptor for receiving said at least one impression element;
guiding said dental implant at said site by manipulating said wrench to which said impression coping and said dental implant are connected;
using said wrench to insert said dental implant into a final position within said jawbone at said site;
removing said wrench from said impression coping;
placing said impression material over said impression coping to create an impression of said site;
removing said impression material; and
removing said impression coping.

81. The method of claim 80, wherein said at least one impression element includes a plurality of impression elements for engaging impression material and holding said impression coping non-rotationally within said impression material, said wrench having a plurality of individual receptors for receiving a corresponding one of said plurality of impression elements and connecting said impression coping to said wrench.

82. The method of claim 81, wherein said plurality of impression elements are disposed in circumferential symmetry around said axis.

83. The method of claim 80, wherein said dental implant is externally threaded and said step of using said wrench to insert said dental implant includes the step of rotating said wrench.

84. The method of claim 80, wherein said wrench includes means for retaining said impression coping therein.

85. The method of claim 80, wherein said impression coping is a pick-up coping and said step of removing said impression coping is accomplished by said step of removing said impression material.

86. The method of claim 80, wherein said impression coping is a transfer coping and said step of removing said impression coping includes the step of unscrewing a screw attaching said impression coping to said implant after said step of removing said impression material.

87. A combination of a coping and a wrench, said coping comprising a body being substantially symmetrical around an axis extending therethrough, said body being attachable at a first end to another component and having an outer surface extending between said first end and a second end which is opposite said first end, said outer surface having a plurality of individual impression interlocking elements on said outer surface, said wrench having a bore being sized to receive said body, said bore including an individual receptor for each of said plurality of impression interlocking elements for locking said wrench and said coping against relative rotation around said axis when said body is resident within said bore.

88. The combination according to claim 87, wherein said wrench includes means to turn said combination of said wrench and said coping around said axis.

89. The combination according to claim 88, wherein said plurality of individual impression interlocking elements are circumferentially symmetric around said axis.

90. The combination according to claim 87, wherein said wrench includes means for releasably retaining said coping within said bore.

91. The combination according to claim 90, wherein said retaining means includes an O-ring within said bore and an annular grove on said coping for interlocking within said O-ring.

92. The combination according to claim 91, wherein said coping includes a bolt for fastening said body to another structure, and said bolt has a head on which said annular groove is disposed.

* * * * *